(12) United States Patent
Nitsche et al.

(10) Patent No.: US 9,268,884 B2
(45) Date of Patent: Feb. 23, 2016

(54) PRODUCTION CONTROL METHOD AND DEVICE FOR CHECKING THE TRAVERSABILITY OF PIPES

(75) Inventors: Stefan Nitsche, Mulheim (DE);
Andreas Groos, Rheurdt (DE);
Xiaoxing Guo, Valenciennes (FR);
Nicolas Nourrit, Le Quesnoy (FR);
Alejandra Segura, Saint Saulve (FR)

(73) Assignee: V & M FRANCE, Boulogne-Billancourt (FR)

( * ) Notice: Subject to any disclaimer, the term of this patent is extended or adjusted under 35 U.S.C. 154(b) by 525 days.

(21) Appl. No.: 13/700,741

(22) PCT Filed: May 30, 2011

(86) PCT No.: PCT/FR2011/000319
§ 371 (c)(1),
(2), (4) Date: Feb. 4, 2013

(87) PCT Pub. No.: WO2011/151538
PCT Pub. Date: Dec. 8, 2011

(65) Prior Publication Data
US 2013/0131856 A1 May 23, 2013

(30) Foreign Application Priority Data

Jun. 3, 2010 (FR) ...................... 10 02351

(51) Int. Cl.
| | | |
|---|---|---|
| G06F 17/50 | (2006.01) |
| G01B 11/10 | (2006.01) |
| G01B 17/02 | (2006.01) |
| G01N 29/04 | (2006.01) |
| G01N 29/28 | (2006.01) |
| G01N 29/30 | (2006.01) |

(52) U.S. Cl.
CPC ............. *G06F 17/50* (2013.01); *G01B 11/105* (2013.01); *G01B 17/02* (2013.01); *G01N 29/043* (2013.01); *G01N 29/28* (2013.01); *G01N 29/30* (2013.01); *G01N 2291/2634* (2013.01)

(58) Field of Classification Search
None
See application file for complete search history.

(56) References Cited

U.S. PATENT DOCUMENTS

| | | |
|---|---|---|
| 5,218,868 A | 6/1993 | Yamazaki et al. |
| 5,596,508 A | 1/1997 | Cuffe |
| 6,091,500 A | 7/2000 | Bahr et al. |

FOREIGN PATENT DOCUMENTS

| | | |
|---|---|---|
| DE | 10 2008 060 391 B3 | 4/2010 |
| EP | 0 444 800 | 9/1991 |
| EP | 0 716 301 | 6/1996 |
| JP | 10-62106 A | 3/1998 |
| JP | 2000-225414 A | 8/2000 |
| JP | 2006-322937 A | 11/2006 |

OTHER PUBLICATIONS

International Search Report Issued Sep. 6, 2011 in PCT/FR11/00319 Filed May 30, 2011.

*Primary Examiner* — Ryan Jarrett
(74) *Attorney, Agent, or Firm* — Oblon, McClelland, Maier & Neustadt, L.L.P.

(57) ABSTRACT

A device for checkivng steel pipes during production and to a method using the device. The device includes a station for acquiring measurement data representative of physical measurements of the geometry of a pipe taken on an outside thereof, and a computer system configured to store template data applicable in a coordinate system and representative of overall geometry of a sizing body. In a chosen coordinate system, the system then provides a three-dimensional representation of parts of the pipe. For each part of the pipe, the system is referenced to determine a critical parameter, representative of the margin of passage of the sizing body inside a chosen part of the pipe. The method and device may thus establish a diagnostic of traversability of the pipe by a sizing body.

15 Claims, 5 Drawing Sheets

Production of steel "rounds"

Manufacture of the pipe

Figures 1, 2:
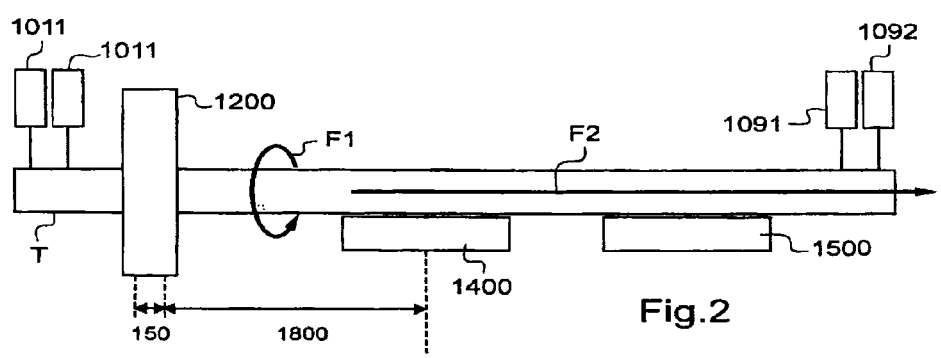

Non-destructive test
(defects)

Straightness test

Installation of the
end connections

Dimensional inspections

Traversability inspection

Decision of the fate (application) of the pipe

Correct    to be inspected    Incorrect

PRODUCTION CONTROL METHOD AND DEVICE FOR CHECKING THE TRAVERSABILITY OF PIPES

The invention relates to an aid to the production control of pipes such as pipes used in oil applications.

Seamless steel pipes are now manufactured particularly for oil drilling and production applications. These pipes have an individual length of the order of 10 m and are interconnected to form one very long pipeline. They are distinguished by the characteristics of their connection as well as by their outside diameter. In their application, however, it is also important to now the clear inside diameter of the pipe, which is often smaller at the end connections measured on the raw production pipe.

Pipe manufacture is subject to different inspection standards, one of which involves being able to pass inside the pipe a sizing body called a "drift", such as a cylinder of well determined diameter and length. This inspection may be conducted throughout the length of the pipe, or only at its ends, where the passage of such a shaft may be more difficult. In the oil sector, the geometry of the calibration shaft and the other test conditions are set out in the standard API 5 CT/ISO 11950.

In practice this presents various difficulties, ranging from the need to provide several sizing bodies with different characteristics to cover a range of pipes, to risk management to ensure that the sizing body does not become stuck inside the pipe.

This invention will improve the situation.

What is proposed first is a method that aids the production control of steel pipes, comprising the following steps:
   a. acquiring measuring data representative of physical measurements of the geometry of a steel pipe taken on the outside thereof,
   b. from these measurement data, generating converted measurement data to form a three-dimensional representation, by pixels, of the inner wall of said pipe, over a longitudinal area of the pipe, said three-dimensional representation being related to a chosen system of coordinates having a point of origin and an axis that are marked relative to the pipe,
   c. preparing template data representative of the overall geometry of a sizing body, these template data being applicable in said chosen system of coordinates,
   d. considering a first section of the pipe for which converted measurement data are available, and determining from these converted measurement data and template data a critical value representative of the margin of passage of the sizing body inside this section of the pipe,
   e. selectively repeating step d/ for other pipe sections offset relative to each other by an overlap, and
   f. establishing a diagnostic of traversability of said longitudinal area of the pipe by the sizing body from critical values obtained in steps d/ and e/, and relative positions of the sections of successive pipes.

According to a particular aspect of the method, the measurement data include measurements relating to the outer circumference of the pipe and measurements relating to its wall thickness taken on a pipe whose movement includes a longitudinal translation.

According to other particular aspects of this method, which may be combined:
   the measurements relating to the outer circumference of the pipe are taken by laser sensors, whilst the measurements relating to its wall thickness are taken by ultrasonic sensors connected to the pipe by a liquid transmission medium.
   the ultrasonic sensors are mounted so that they are floating in order to remain in interaction with the pipe, and a system is provided for measuring the relative positions of the laser sensors and ultrasonic sensors.
   simultaneously the measurements relating to the outer circumference of the pipe and the measurements relating to its wall thickness are taken by ultrasonic sensors interacting with a water box traversed by the pipe.
   in step c/ the template data comprise an overall outside diameter of the sizing body,
   step d/ comprises the following sub-steps:
      d1. determining a cylinder inscribed inside the pipe section, and
      d2. determining the difference between the diameter of the inscribed cylinder and the overall diameter of the sizing body, as a critical value,
   step e/ comprises, for each pair of adjacent pipe sections, the establishment of the possibility of the passage from one section to the next from said critical value, of the angular deviation between the axes of the two pipe sections, and at least one longitudinal dimension of the sizing body.
   Provision is made for determining a straight-line generating shape which is inscribed inside the inner surface of the pipe, section by section, and testing whether the sizing body passes into the straight-line generating shape of each section considered.

Also proposed is a device aiding the dimensional inspection of steel pipes during production, comprising:
   at least one measuring station arranged to acquire measurement data representative of physical measurements of the geometry of a steel pipe taken on the outside thereof, and
   a computer system capable:
      of storing template data representative of the overall diameter of a sizing body, these template data being applicable in said chosen system of coordinates,
      from measurement data, generating converted measurement data to form a three-dimensional representation, by pixels, of at least two pipe sections offset relative to each other with an overlap, this three-dimensional representation being related to a chosen system of coordinates having point of origin and an axis marked relative to the pipe,
      for each pipe section, determining from its converted measurement data and template data a critical value representative of the margin of passage of the sizing body inside this pipe section, and
      establishing a diagnostic of the traversability of the pipe sections by the sizing body from said critical values and relative positions of the pipe sections.

According to a particular aspect of the device, measurement data comprise measurements relating to the outer circumference of the pipe and measurements relating to its wall thickness taken on a pipe whose movement comprises a longitudinal translation.

According to other particular aspects of this device, which may be combined:
   the device comprises a laser measuring station for the measurements relating to the outer circumference of the pipe, and an ultrasonic sensor station, connected to the pipe by means of a liquid transmission medium, for the measurements relating to the wall thickness of the pipe, the device is of the type in which the ultrasonic sensors are mounted so that they are floating so that they remain in interaction with the pipe, and provision is also made for a system that measures the relative positions of the laser and ultrasonic sensors.

simultaneously the measurements relating to the outer circumference of the pipe and the measurements relating to its wall thickness are taken by a measuring station comprising ultrasonic sensors interacting with a water box traversed by the pipe.

the template data comprise an overall outside diameter of the sizing body, the determination of the critical value includes the search for a cylinder inscribed inside the pipe section, and the determination of the difference between the diameter of the inscribed cylinder and the overall diameter of the sizing body, as a critical value, the establishment of the diagnostic comprises, for a pair of adjacent pipe sections, the establishment of the possibility of the passage from one section to the next on the basis of said critical value, of the angular deviation between the axes of the two pipe sections, and of at least one longitudinal dimension of the sizing body.

Provision is made for determining a straight line generating shape which is inscribed inside the inner surface of the pipe, section by section, and testing whether the sizing body passes into the straight line generating shape of each section considered.

Figure 3:
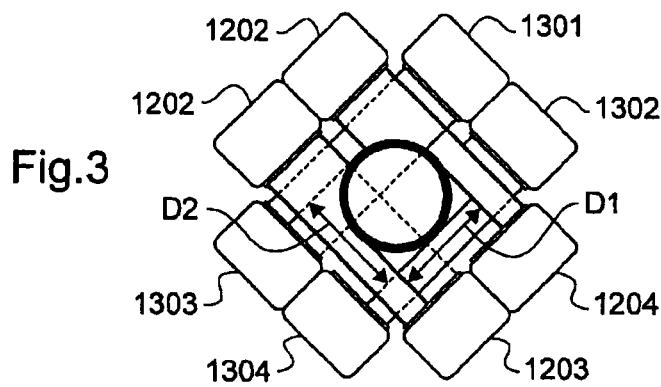
Figure 4:
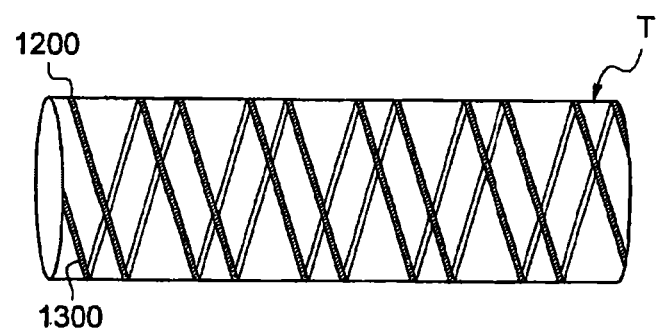
Figure 5:
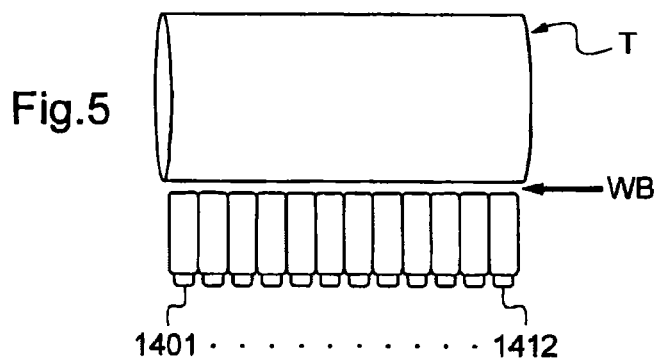
Figure 6:
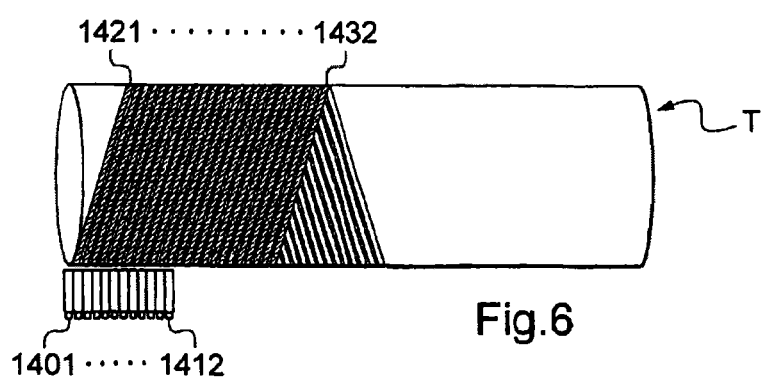
Figure 7:
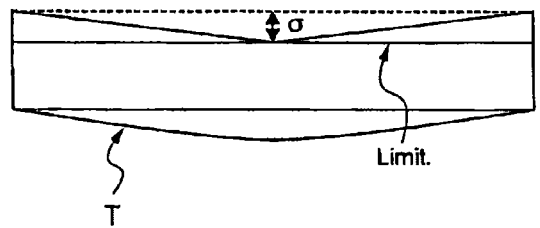
Figure 8:
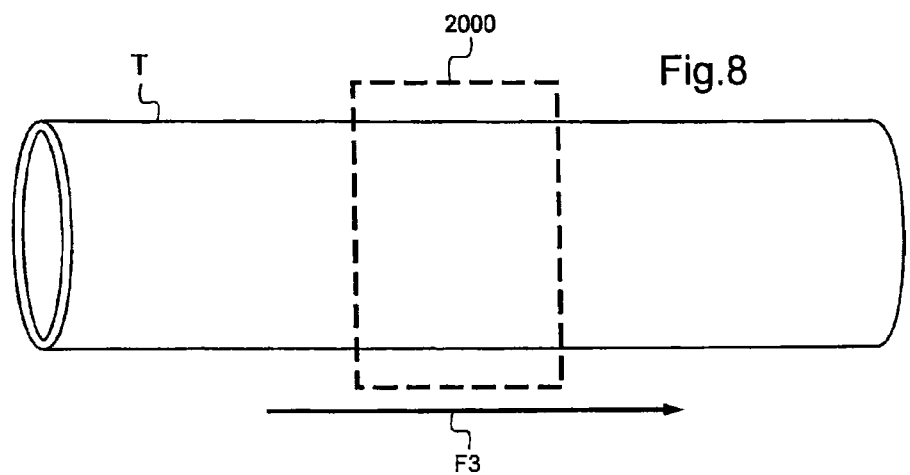
Figure 9:
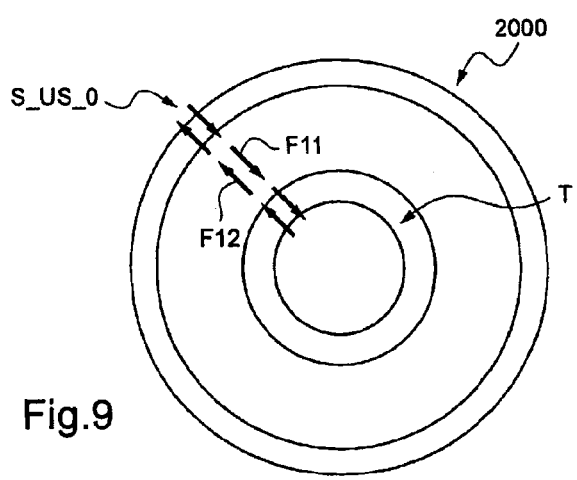
Figure 10:
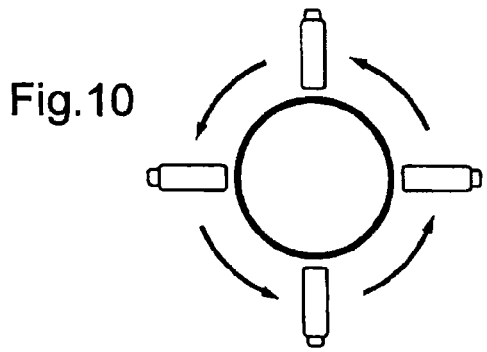
Figure 11:
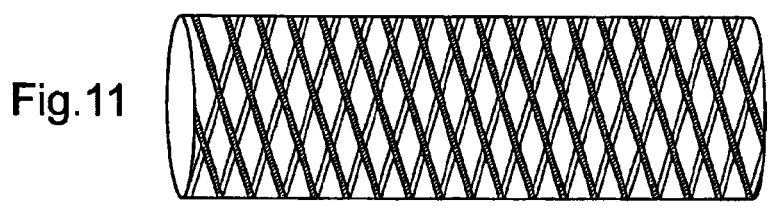
Figure 12:
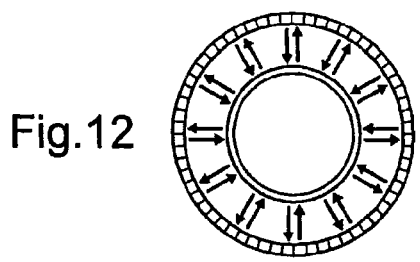
Figure 13:
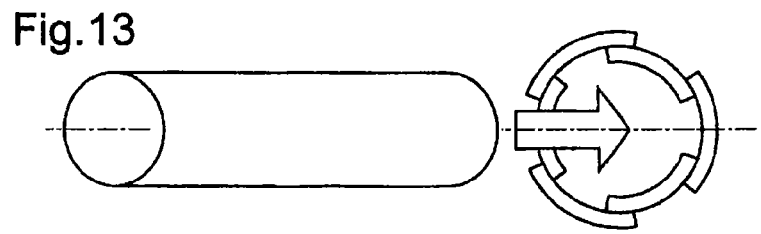
Figure 14:
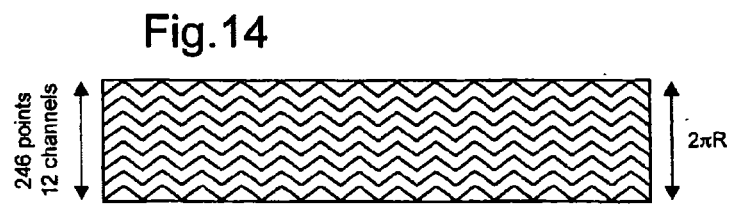
Figure 15:
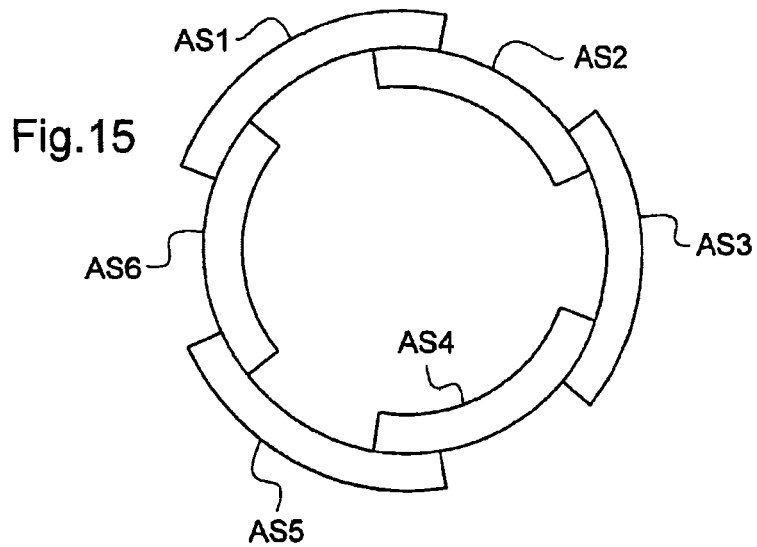
Figure 15A:
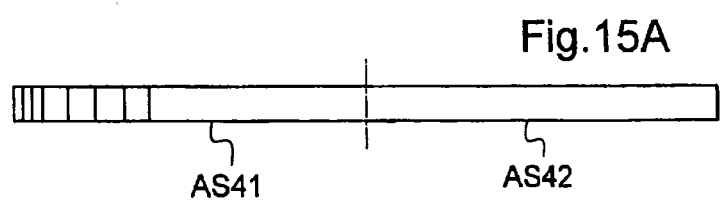
Figure 16:
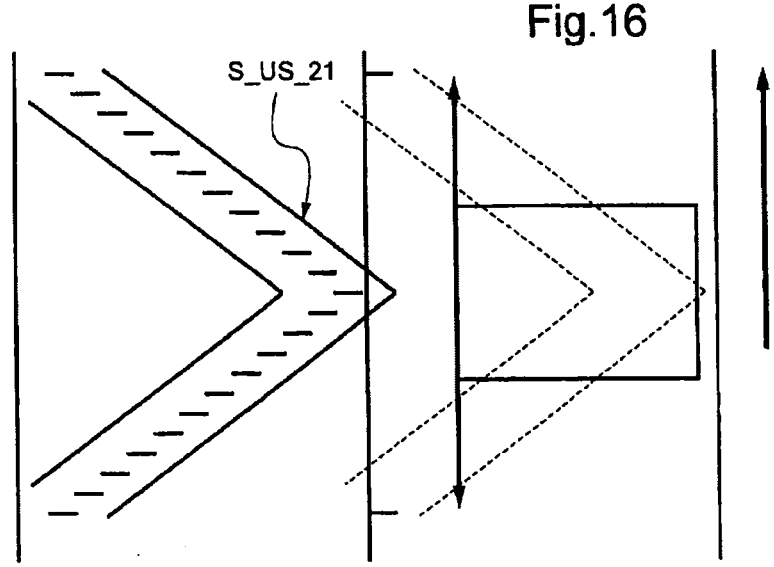

Other characteristics and advantages of the advantage will become apparent from the following description and from the attached drawings, in which:

FIG. 1 is the general explanatory diagram of a method of production of a steel pipe, FIG. 2 is the explanatory diagram of a test pipe installation according to a first embodiment, FIG. 3 is a more detailed diagram of element 1200 in FIG. 2, FIG. 4 illustrates the distribution of the measurements of element 1200 along the pipe, FIG. 5 is a more detailed diagram of element 1400 in FIG. 2, FIG. 6 illustrates the distribution of the measurements of element 140 along the pipe, FIG. 7 illustrates the longitudinal section of a pipe section, with notations on the curvature of the pipe, FIG. 8 is the explanatory diagram of a test pipe installation according to a second embodiment in which the pipe traverses a water box 2000, FIG. 9 is the explanatory diagram of a pipe traversing a water box of a first type, FIG. 10 is the explanatory diagram of a pipe traversing a water box of a second type, with rotating ultrasonic sensors, FIG. 11 illustrates the distribution of the measurements of the sensors in FIG. 10 along the pipe, FIG. 12 is the explanatory diagram of a pipe traversing a water box of a third type with fixed ultrasonic sensors, FIG. 13 illustrates a convention of representation of the sensors in FIG. 12, FIG. 14 illustrates the distribution of the measurements of the sensors in FIG. 12 along the pipe, FIG. 15 illustrates a particular embodiment according to the convention in FIG. 13, FIG. 15A illustrates a detail in FIG. 15, FIG. 16 illustrates in detail part of the distribution of the measurements of the sensors in FIG. 15 along the pipe.

The drawings and appendices to the description comprise elements of a particular nature. They may therefore not only serve to provide a better understanding of the description, but they also contribute to the definition of the invention, whichever the case.

Reference is now made to FIG. 1, which illustrates diagrammatically the complete process of manufacturing a pipe, e.g. for application in oil wells. The steps are not necessary in the order given, and some may be carried out simultaneously.

The first step 10 is the manufacture of a solid steel pipe which is called "round" in the relevant art.

A seamless pipe is then manufactured in step 11, by hot rolling/extrusion on a mandrel, or on a pear bore mounted at the end of a rod which passes into the axis of the pipe.

Step 12 comprises non-destructive tests to locate any defects in the pipe. These non-destructive tests may assume different forms making use of ultrasound, for example, or even Foucault currents.

Step 13 then involves an inspection of the straightness of the pipe. This inspection may be carried out manually with a rule or by using a laser. In the oil sector the straightness criteria are established in the aforementioned standard API 5 CT/ISO 11950

After this step 14 consists in threading the two ends of the pipe, generally one male, the other female. This can be done, for example, by direct tapping directly at both ends of the pipe, i.e. by the addition of end ferrules pre-threaded onto the same. Certain pipes intended to be joined by welding cannot be threaded.

Other dimensional inspections may be carried out in step 15.

This is followed, in step 16, by a "traversability" inspection which verifies that a sizing body with well defined characteristics is able to traverse the pipe either from end to end or more simply on one or more pipe segments. The most common method is to work on two end segments where the diameter may be reduced by the application of the threaded connections.

After step 16 a decision is taken on what to do with the pipe in step 17. This decision depends on the results obtained from step 16. Consideration may also be given to problems encountered in the previous steps (mainly 12, 14 and 15), if these problems have not resulted in the immediate removal of the pipe, before arriving at step 16. In step 17 it may be decided to qualify the pipe as correct or, on the other hand, to qualify it as incorrect or, in an intermediate situation of uncertainty, it may be decided to proceed with other inspections on the pipe, e.g. manual inspections.

The present invention concerns essentially step 16, as well as the decision following step 17. However, as will be seen, these steps are not independent of what has previously taken place, e.g. during the straightness inspection of the pipe.

The applicant is interested in the dimensional inspections carried out in step 15.

A first embodiment is now considered.

The installation which carries out the dimensional inspections on the pipe is of the type illustrated in FIG. 2. The pipe is illustrated diagrammatically in T.

In this embodiment the pipe advances, coaxially on itself, following a helical movement which is analysed as a rotation (represented diagrammatically by arrow F1), accompanied by a translator movement along the longitudinal axis of the pipe (represented diagrammatically by arrow F2).

At the inlet are arranged two laser speedometers 1011 and 1012 for measuring the axial and circumferential speeds of passage of the pipe.

After the laser speedometers 1011 and 1012 is installed a station 1200, which will measure the outside diameter of the pipe. This is followed by two ultrasonic measuring stations 1400 and 1500 installed along the route of the pipe, being connected to the pipe by a continuously maintained layer of water which may be referred to as a "water bed". At the other end two other laser speedometers 1091 and 1092 may be provided, operating as laser speedometers 1011 and 1012. This option enables the measurements to continue at the end of the pipe passage, when laser speedometers 1011 and 1012 no longer see the pipe.

The invention is based on the concept that there is no provision for a station specifically dedicated to traversability inspection, in which a sizing body would be physically passed through the inside the pipe. On the other hand, the traversability inspection will be carried out virtually, i.e. it makes use, essentially, of the measurements already taken on the pipe for other reasons, these measurements being arranged so that the traversability inspection can be carried out.

The station comprising the inlet laser speedometers 1011 and 1012 will now be described.

One of them, for example laser speedometer 1011, transmits a laser beam to the pipe from the outside, at a selected angle, in a radial plane. For the sake of simplification, it may be considered that the radiation backscattered by the pipe is mixed (heterodyne) with the gross radiation from the laser in order to indicate the Doppler frequency deviation in an optical sensor.

Work is preferably done in the so-called "differential Doppler" mode, with two laser beams arriving symmetrically on the pipe in a radial plane, whilst the optical detection is made along a perpendicular to the surface of the pipe. Knowing the laser wavelength and the angle of incidence φ of the laser beams on the pipe at various points in the direction of detection, the Doppler frequency deviation $f_D$ can be converted to an axial speed value V of the pipe, for example in meters per second, according to the formula:

$$V = (f_D \lambda)/(2 \sin \phi).$$

The other speedometer, 1012 for example, uses two laser beams arriving symmetrically on the pipe in an axial plane, whilst the optical detection is made along a perpendicular to the surface of the pipe. As previously, the Doppler frequency deviation obtained is converted to a value of the circumferential speed of the pipe, e.g. in meters per second. In a particular embodiment, the inlet laser speedometers 1011 and 1012 are articulated to the LSV-300 equipment from the German company Polytec GmbH.

The diameter measuring station 1200 is illustrated in greater detail in FIG. 3. It comprises two light transmitters 1201 and 1202, placed side by side in a known position. Light transmitters 1201 and 1202 are positioned so that two essentially flat, rectilinear light beams are established in the direction of the respective light detectors 1203 and 1204, also in a known relative position. Such a flat beam may be created from a laser beam disseminated through a cylindrical lens. The photodetectors are, for example, photo diode bars.

The two light beams are positioned essentially adjacent to each other, in the same plane, so that
- these light beams are intercepted by the pipe on the side on which they are adjacent (inside), whilst
- on the outside each beam always exceeds the large diameter of the pipe.

The respective light detectors 1203 and 1204 are positioned so that they "see" the two transversally opposite areas where the pipe intercepts the beam of light. In the embodiment the mounting of elements 1201, 1202, 1203 and 1204 has two planes of symmetry which pass through the axis of the pipe, but this is not essential. Moreover, the two light transmitters 1201 and 1202 could be combined into one, and similarly, the two light detectors 1203 and 1204 may also be combined into one.

Detectors 1203 and 1204 will therefore receive those parts of the incident beams which exceed the pipe. The positions of light detectors 1203 and 1204 being known, their unlit parts (or, by subtraction, their illuminated parts) allow access for measurement of the outside diameter D1 of the pipe.

Provision is preferably made for another similar arrangement, at right angles to the first arrangement, comprising light sources 1301 and 1302, with at the opposite end light sensors 1303 and 1304. This enables another diameter D2 to be obtained in the direction perpendicular to that of diameter D1. In a particular embodiment diameter measuring station 1200 is based on the product LMD 412-DSP from LAP lasers GmbH.

Briefly, two diameter measurements are therefore obtained in both directions perpendicular to each other, located in the same plane, in a straight section of the pipe. On each occasion the direction of measurement of the diameter is perpendicular to the direction of the parallel plane light beam used.

As the pipe advances by a translational movement accompanied by a rotation, the points of diameter measurement will follow two helices or spirals, as illustrated in 1200 and 1300 on the diagrammatically represented pipe T in FIG. 4. The two helixes are essentially at right angles to each other relative to the longitudinal axis of the pipe, since the measurements in the two perpendicular directions are taken at the same time and therefore in the same plane in a straight section. (Otherwise they would be offset relative to this situation at right angles, in proportion to the time lag between the two measurements). It will be observed that with two diameter measurements of the pipe in a radial plane, four points of the circumference are obtained for which the diameter is known. In fact, one diameter measurement is valid for each of the ends of this diameter. To the two helices shown in FIG. 4 are therefore added, on the basis of the same measurements, two other helices which are diametrically opposite them. The periphery of the pipe is therefore covered by four "diameter helices".

More detailed characteristics of these measurements are given in Table 1 below.

TABLE 1

| Characteristics | Value |
| --- | --- |
| precision of the photodetectors | 10 micrometers |
| useful precision | 10 micrometers |
| pitch of one coil of a helix | 120 mm (Pipes with an outside diameter of 200 to 400 mm approximately) |
| measuring pitch along the axis of the pipe | 1 mm |
| rate of measurement | 120 points per coil and laser |
| number of measuring points per coil (2 times 2 helices) | 4 * 120 = 480 |

After station 1200 in FIG. 2 an ultrasonic measuring station 1400 is provided. Another ultrasonic measuring station 1500 may also be provided downstream. For example, ultrasonic station 1400 performs pipe thickness measurements and the detection of longitudinal faults, whilst ultrasonic station 1500 detects transverse and oblique faults.

The pipe thickness measurement by station 1400 will also serve to measure traversability.

A more detailed diagram of station 1400 is shown in FIG. 5. Here we can see a cross-section of pipe T, represented diagrammatically. A water bed WB is arranged continuously between the lower section of the pipe and twelve ultrasonic sensors, referenced 1401 to 1412, positioned side by side in the direction of displacement of the pipe. Each sensor extends transversally along the arc of a circle in a straight section under the pipe. In a particular embodiment station 1400 is based on the product GRP-PAT-PB from General Electric Inspection Technologies (GEIT).

Each ultrasonic sensor measures the wall thickness of the pipe in a straight section at its level. The principle of this ultrasonic measurement is of prior art. It uses the time lag between the echo obtained on the outer wall of the pipe across the water bed, and the first echo that follows, which corresponds to a reflection (or backscatter) of the ultrasounds on the inner wall of the pipe. At a given moment 12 points of thickness measurement are obtained in 12 straight sections spaced along the axis of the pipe. The 12 points of measurement will follow the twelve helices 1421 to 1432, taking account of the rotation and translation of the pipe. We therefore have 12 "thickness helices".

More detailed characteristics of these measurements are given in Table 2 below.

TABLE 2

| Characteristic | Value |
|---|---|
| resolution of the ultrasonic measurement | 0.01 mm |
| useful precision | 0.03 mm |
| pitch of one coil of a helix | 120 mm |
| axial spacing of the ultrasonic sensors | 10 mm |
| number of measuring points per coil | 1100 to 1500 points/coil |

Finally, the station comprising outlet laser speedometers 1091 and 1092 operates as inlet laser speedometers 1011 and 1012. In a particular embodiment laser speedometers 1011, 1012, 1091 and 1092 are articulated to the LSV-300 equipment from the German company Polytec GmbH.

Since the pipe is rigid the axial speed measurements at 1011 and 1091 must be the same at the same time. We therefore know in real time the exact speed of axial displacement of the pipe. One procedure for this is to transmit a signal whenever the pipe has advanced 20 mm, for example.

On the other hand, the circumferential speed measurements at 1012 and 1092 may be slightly different because the diameter of the pipe at station 1092 may be slightly different from its diameter at station 1012. Moreover, the position of these stations 1011, 1012, 1091 and 1092 along the axis of translation of the pipe is known. If all the circumferential speed measurements of stations 1012 and 1092 for a pipe have been memorised, it is possible, a posteriori, to construct pairs of two measured circumferential speed values corresponding to the same straight section of the pipe.

From another point of view, even if the diameter of the pipe at station 1092 may be slightly different from its diameter at station 1012, it remains true, however, that the angular velocity of the pipe at station 1092 is the same as at station 1012 since the pipe is rigid. The diameter tolerance is also known. Consequently we can start from the average of the two circumferential speed measurements obtained at 1012 and 1092. We may deduce from this the angular velocity taking into account the diameter and diameter tolerance. This is acceptable because the angular velocity varies little from one angular measurement position to the next due to the inertia of the pipe in one complete revolution. In real time this makes it possible to transmit a signal whenever the pipe has performed one complete revolution.

We now start with this case where stations 1011, 1012, 1091 and 1092 supply in real time a "rotation" signal whenever the pipe has performed a complete revolution on the one hand, and a "translation" signal whenever the pipe has advanced 20 mm on the other.

The position of the straight measuring sections associated with ultrasonic sensors 1401 to 1412 is known. We also know the axial distance between stations 1200 and 1400 (more precisely the distance between two straight respective reference sections of stations 1200 and 1400). Here it is 1800 mm. For technical reasons the plane of the straight working section of station 1200 (for diameter measurement) may be either the plane defined by the dotted line which rises to the right in station 1200, or the plane of the dotted line which rises to the left. The choice of plane depends on the nominal diameter of the pipe. In both cases the straight diameter measurement section is precisely known.

We therefore have a good knowledge of the axial offset between the straight sections associated with ultrasonic sensors 1401 to 1412 and the straight section of the diameter measurements.

By also using the rotation and translation signals we can therefore approximately reset the diameter and thickness measurements relative to the surface of the pipe. In other words we can approximately reset the four "diameter helices" and the 12 "thickness helices" relative to the pipe.

However, in order to be able to reset the four "diameter helices" and the 12 "thickness helices" accurately it would be necessary to have a point of reference on the pipe which could be related to these two groups of helices. This is not the case here.

It would therefore be necessary to initiate the exact times of the ultrasonic firing according to the rotation and translation signals. In other words it would be necessary for the clocks which trigger the diameter and thickness measurements to be synchronised in real time. The applicant has observed that this is not necessary because without this synchronisation it is already possible to work with a positioning error of less than 1 mm in both directions.

On the other hand the axial speed of displacement of the pipe is known precisely in real time. And its circumferential (or angular) velocity is also precisely known in terms of a mean value over one revolution.

The distance which the pipe covers from one station to the next is known. Its axial speed is known. We can therefore determine time Tx taken by the pipe to move from one station to the other.

We therefore know the time lag between the 4 "diameter helices" for them to be reset on the same straight section of the pipe as the 12 "thickness helices". Once this is done, however, the angular resetting of all these helices in the straight section is not certain because the angular velocity of the pipe has been able to vary for the time Tx.

Ideally it would be necessary, in the straight section of the pipe, for a measured value of the diameter to be located exactly in the same radial direction as a measured value of the wall thickness in order to be able to calculate the difference, thereby obtaining the inside diameter of the pipe. The applicant has observed that is still possible to calculate the inside diameter of the pipe from values of the outside diameter and thickness which are slightly offset from one another, angularly and/or axially, by using the fact that the surface of the pipe is continuous. In other words, the applicant has observed that the inside diameter can be calculated provided that there are outside diameter measuring points and thickness measuring points which are sufficiently close to one another so that the local variations in the outside diameter of the pipe, its wall thickness and its eccentricity remain sufficiently small in relation to the accuracy required for the inside diameter measurement. In a particular installation the applicant has proceeded to calibrate the installation from a pipe all of whose measurements were known. He then determined the effect of the circumferential dispersal on the dispersal (variation) in the inside diameter calculation, which is considered to be compatible with the required accuracy.

In one example we consider a 12 m pipe travelling at a pitch of 120 mm with 12 coils per revolution. A total of 12*1200/120=1200 coils are obtained in the thickness measurement.

In the diameter measurement we have an ordered series of values of the inside diameter $D_i$ of the pipe, covering the latter with a high resolution. We have, for example, 360 $D_i$ values per coil for 400 cols per pipe.

A first method of evaluating the traversability of the pipe by a cylinder of diameter $D_{drift}$ will now be described. The process is performed in principle on a pipe which has not yet been provided with its end connections/threads.

First of all the pipe is cut up virtually into a succession of sections. These sections preferably overlap at least 50%, for example, preferably up to 90%.

A calculation and processing procedure is then performed for each of the virtual sections of the pipe. This process may involve all or some of the following steps:
1. Recover the ordered set of values of the inside diameter $D_i$ corresponding to the section considered.
2. For each coil, compare its inside diameters to determine the lowest value, or minimum inside diameter. (This step, which is optional here, may be used below).
3. Correct the inside diameter values as a function of an out-of-plumb of the pipe, designated σ. This value σ may correspond to the maximum permissible deflection for the section of pipe T, taking into consideration the applicable manufacturing standards, as illustrated in FIG. 7.
4. For oil pipes, the aforementioned standard distinguishes the deflection $σ_{centre}$ for the intermediate sections and the deflection $σ_{ends}$ for the end sections.
   In a variant, a measured value σ could be taken on the current section during the tests in step 13 shown in FIG. 1.
4. For each coil its minimum inside diameter is taken, and if the minimum inside diameter $D_{min}$, reduced by the out-of-plumb σ (preferably incorporating a small margin) is greater than (or equal to) the diameter $D_{drift}$, this coil is then traversable; otherwise this coil is noted as one of the positions in which the sizing body would become stuck.
5. If all the coils are traversable (with $D_{min}-σ≥D_{drift}$ at all points), the sizing body then passes through; otherwise it does not and the positions of the coils in which the sizing body would become stuck are known (by step 4).
6. In a variant, or as a supplement, the largest sizing body that can traverse the pipe can also be determined. For this purpose the values $D_{min}-σ$ are compared with all the coils of the pipe. The lowest value of $D_{min}-σ$ represents the largest sizing body diameter that can fit.

Therefore $D_{min}-σ$ a serves as the critical value representative of the margin of passage of the sizing body inside each section of the pipe.

The above relates only to the passage of the sizing body in diameter. In addition it has a certain length which may cause a problem to a greater or lesser extent, depending on the straightness defects of the pipe. The length and overlap of the sections are chosen to take account of the length of the sizing body.

In other words, we know the distribution of the inside diameters of the pipe in space, along the pipe, but we do not know the exact positions of the centres of the coils having these diameters. The API straightness test has ascertained that the pipe has a curvature that is less than the maximum permissible curvature. We may therefore take this maximum permissible curvature as a starting point to compensate for the fact that we do not know the exact positions of the centres of the coils. The "limit" lines in FIG. 7 indicate the limits in diameter for a straight-line passage, the curvature of the pipe being highly exaggerated.

The pipe is considered to be traversable along its entire length if all the sections examined are traversable by the sizing body. The pipe considered non-traversable if one section examined is completely blocked. If one or more sections examined are at the sticking limit, the pipe must be "inspected".

A second embodiment is now considered.

This may apply to pipe production installations in which pipe T traverses a water box 200, illustrated by a dotted line frame in FIG. 8. In this case the pipe is generally subjected to a pure translation movement, as defined by arrow F3, although a helical movement is also possible.

FIG. 9 shows the principle of measurement in water box 2000. Consideration is given to an ultrasonic sensor, denoted for convenience by S_US_0. Pipe T passes through the inside of water box 2000. The sensor transmits a pulsed ultrasonic beam, essentially radially towards the pipe (Arrow 11—outward). This is followed by a first ultrasonic reflection through the outer wall of the pipe (Arrow 11—return), hence a first beam reflected back to the sensor (outer wall echo). Some of the incident ultrasonic beam penetrates the pipe (arrow 12—outward), followed by a second ultrasonic reflection through the inner wall of the pipe (Arrow 12—return). And part of this second reflected beam passes back through the outer wall to return to sensor S_US_0. This is the first inner wall echo.

In practice this type of measurement is taken throughout the periphery of the pipe. This may be done with revolving ultrasonic heads, e.g. four in number, as illustrated in FIG. 10. This is a water box of the type known as "ROT180VIS" from GEIT. In this case, because the pipe is advancing, measurements are again obtained along helices, as indicated diagrammatically in FIG. 11.

The principal axis of symmetry of the ultrasonic beam transmitted is known, and is in principle perpendicular to the crown of ultrasonic sensors, such as S_US_0. From the time of outward-return propagation for the first inner wall echo observed by ultrasonic sensor S_US_0 we can determine the position of the point of reflection on the inner wall of the pipe relative to a point of reference on sensor S_US_0. This is a three-dimensional position taking into account the movement of the pipe. The position of the point of reflection on the inner wall of the pipe may then be related to a point of origin in space, for example the centre of the crown of ultrasonic sensors.

It is currently preferred to use the phased arrays of ultrasonic sensor encircling the pipe. The principle of this is illustrated in FIG. 12. This consists, for example, of a water box of the type known as "ROWA 240 SK 12957" from GEIT. By scanning the excitation of the ultrasonic sensor measures are obtained which are technically similar to those of the revolving ultrasonic heads.

In practice the ultrasonic sensors may be distributed around the arcs of circles, offset alternately along the axis of the pipe, and are partially overlapped (FIG. 13). They are also excited alternately to avoid, in particular, interferences between ultrasonic beams. This is followed by a sawtooth distribution of the measuring points on the periphery of the pipe, as illustrated in FIG. 14.

It is this embodiment which will now be described in more detail.

FIG. 15 illustrates the positions of six sensor arcs AS1 to AS6, distributed around the circumference of the pipe, with overlap. Here too arcs AS2, AS4 and AS6 are shown on the inside, radially, of arcs AS1, AS3 and AS5. This is a drawing convention used to show their overlap. In fact, arcs AS2, AS4 and AS6 are positioned on the same radius as arcs AS1, AS3 and AS5, but offset axially from them.

Each arc of sensors comprises 2 semi-arcs of sensors AS41 and AS42, comprising 64 sensor elements each. Virtual sensors are defined by combining the signals from several physical sensors. The operation will be carried out, for example, according to several methods using 14 to 28 virtual sensors per semi-arc, i.e. 28 to 56 virtual sensors per complete arc. The number of virtual sensors per complete arc is denoted by N.

Therefore around the circumference of the pipe we may use up to six times N virtual transducers, which corresponds to 336 measured values for N=56. In fact, the arcs overlap a little along the circumference of the pipe. The number of different measured values is therefore slightly less.

Reference is now made to FIG. 15A, which details the arc of ultrasonic sensors AS4, which breaks down into two parts AS41 and AS42. The data from these two parts are collected on one and the same measuring channel. These two parts AS41 and AS42 form the two times 64 elements already mentioned for N virtual transducers.

With regard to this FIG. 15A, FIG. 16 indicates the distribution of the pulsed shots of ultrasonic energy, as a function of time, and consequently of the longitudinal displacement of the pipe. The longitudinal speed is typically one meter/second. This provides a better understanding of the sawtooth structure of the above-mentioned measurements. It is observed that the tip of the sawtooth corresponds to the median tank ultrasonic transducer among the N virtual transducers.

In this second embodiment the outside diameter and thickness measurements of the pipe are taken, by design, essentially at the same point, or at points very close to each other. In all cases the position of each point of reflection of the ultrasounds on the inner wall of the pipe may be related to a point of origin in space, for example the centre of the crown of ultrasonic sensors, or the centre of rotation of the revolving ultrasonic heads, or the centre of the arcs of sensors.

In this case the calculation and processing process described above can obviously be used, in reference to FIG. 7. But it may be possible to proceed otherwise, as will now be seen.

In the different cases described above for the second embodiment, we can reduce the measurement to an assembly of M coils for one pipe section. An index i (from 0 to M−1) is considered with is a coil number corresponding to a time, and consequently to an axial displacement of the pipe (possibly accompanied by an angular displacement of the pipe).

On the basis of the raw measurements of the ultrasounds in the water box (or equivalent) we have N measurements per coil. An index j (from 0 to N−1) is considered which is a number of the measuring point in the coil. Strictly speaking, in a case such as that of the water box with revolving ultrasonic heads shown in FIG. 10, or in phased arrays, the different measurements of a coil are obtained sequentially in time (at least in part). We can therefore also assign a time to them, and consequently an axial displacement of the pipe (possibly accompanied by an angular displacement of the pipe). Whatever the type of ultrasonic measurements, the correspondence between index j and this time, as well as the angle of the measurement in the straight section of the pipe, are known.

We therefore have from the start position measurements Mij of the inner wall of the pipe, which may be expressed in the reference system for the crown of ultrasonic sensors, for example in an orthonormal coordinate system whose origin is the centre of the crown of ultrasonic sensors. These are 3D measurements, but they may be reduced to 2D measurements for the same coil, for the measurements of the same coil lie more or less within the same straight section of the pipe.

It is understood that the coil is wound along the pipe in the manner of a helix. The small dimension of the coil along the axis of the pipe is compensated for by projecting it orthogonally in a plane perpendicular to the axis of the pipe. This consists in omitting, for the tips of the coil, the coordinate along the longitudinal axis of the pipe. The number of the coil is sufficient to define the position of its tips along the longitudinal axis of the pipe, to the required precision.

For each coil i of the pipe the position of a central point Ci is first determined, for example in the reference system for the crown of ultrasonic sensors. For this purpose the centre of the circle sought, optimally adjusted to the points of the coil considered. In other words, i being fixed, point Ci is sought for which we have a minimum of $$j\Sigma(Mij - Ci)^2$$

where Mij and Ci are position vectors in the plane of projection.

The measurement vectors Mij are then converted so that they are related to this centre Ci. A table of measurement vectors is therefore obtained denoted by Rij (i=number of the coil, j=number of the point), for which, in each coil, the relative position of each point on the inner surface of the pipe is related to centre Ci.

If there are N recording points of the inner wall of the pipe at each coil (with N even), the inner surface of the pipe may be represented by N/2 traversing segments which will also be called "quasi-diameters". In the space a traversing segment is defined by the position of its ends. The segment of row k has end denoted by Rik and another end, essentially opposing it, denoted by Ri(N/2+k−1). It passes through centre Ci. Therefore the traversing segment is defined by the half-segment which runs from Rik to Ci, followed by the half-segment which runs from Ci to Ri(N/2+k−1). The two half-segments are not exactly aligned with each other, except when the two ends are exactly opposite one another.

In a simplified notation the traversing segment of row k is denoted by Dik (with i=number of the coil, k=row of the segment, running from 0 to N/2−1). Therefore each quasi-diameter Dik connects two points of the inner surface of the pipe positioned essentially 180° to each other and passing through the centre of coil Ci.

We then consider a series of quasi-diameters which are essentially parallel with each other, on all the coils, for example from a first quasi-diameter in the first coil. This is then repeated with all the diametric directions that exist in the first coil. (Even if a quasi-diameter is a slightly broken line, it can nevertheless be assigned a direction, the so-called diametric direction).

In other words, the pipe section is broken down into several sub-assemblies of quasi-diameters, each of which is associated with a respective diametric direction. Each sub-assembly contains the quasi-diameters that are parallel with each other, on all the coils, at the rate of one per coil, so that each quasi-diameter can be assigned to its coil number. The simplest method is to use a table in which the quasi-diameters are indicated in the order of the coils. We call this a "2D plane". A quasi-diameter is defined by the positions of its ends [Rik, Ri(N/2+k−1) in the plane in which the coil to which it belongs is projected, and by its coil number i (or other identifier).

If the pipe section studied has a length of M coils we will have a set (denoted by Pn, n=number of the plane, from 0 to N/2) of N/2 2D planes, each of which comprises M quasi-diameters essentially parallel with each other.

For example, plane $p_0$ will consist of the quasi-diameter $D_{00}$ in coil 0 (i=0), from $D_{1j}$, which is the quasi-diameter essentially parallel with $D_{00}$ in coil 1, ..., from Dij', which is the quasi-diameter essentially parallel with $D_{00}$ in coil i, ..., from $D_{Mj}$ ..., which is the quasi-diameter essentially parallel with $D_{00}$ in coil M. The quasi-diameters are therefore superimposed on each other, in the order of the coils (along the longitudinal axis of the piper), taking into account the position of their ends in each of the planes of projection of the coils.

In other words, data table Rij is updated so that it corresponds to the quasi-diameters that are essentially parallel with each other, from one coil to the next, for all the coils. It is recalled that the correspondence between index j and the radial direction in which the measurement is taken, in the straight section of the pipe, is known.

In each of the 2D planes the trapezium which is tangentially inscribed in the quasi-diameters, on the inside, is sought. A simple method of doing this is as follows:

First lateral side of the trapezium
  Determine a first straight line that connects a first end of the quasi-diameter of the first coil at the end located on the same side in the last coil;
  If this first straight line passes through to the inside of all the other quasi-diameters between the first coil of the last line, it is included;
  Otherwise it is displaced towards through to the inside so that it passes to the inside of all the quasi-diameters.
Second lateral side of the trapezium
  Determine a second straight line that connects the second end (opposite the first) of the quasi-diameter of the first coil, at the end located on the same side in the first coil;
  If this second straight line passes through into the inside of all the other quasi-diameters, between the first coil of the last line, it is included;
  Otherwise it is displaced towards the inside so that it passes through into the inside of all the quasi-diameters.

The first and second straight lines therefore form the two lateral sides of the trapezium, which can be closed at the ends on two parallel sides (virtually).

A cluster or carousel of trapeziums is then obtained covering progressively the different directions around the longitudinal axis of the pipe section.

From these different trapeziums we then obtain a shape with straight generating lines (the lateral sides of the trapeziums), which is inscribed inside the inner surface of the pipe section. It is then determined whether the sizing body passes into this shape with straight generating lines. For this purpose it is sufficient to check whether and how the straight section of the cylindrical sizing body passes through each of the two ends of the shape with straight generating lines. In fact, the minimum passage is at one of the ends for each trapezium.

It may happen that the straight section of the sizing body passes to the two ends but the position of its centre when it passes to one end is offset relative to the position of its centre when it passes to the other end. The angle of the line which joins these two centres, relative to the axis of the pipe, is denoted by α. It is therefore elliptical. The test for passage to the two ends of the shape with straight generating lines is then repeated with this oblique, elliptical section. Repeating this several times may be necessary, for example until the offset between the centres no longer varies.

The test for passage to the ends is carried out with a safety margin which can be determined experimentally. It is a priori much narrower than the aforementioned margin α. The critical value of the test includes in this case the distances between the shape with straight generating lines and the straight (or oblique) section of the sizing body, with the safety margin.

From that point it is possible to establish the diagnostic of the traversability test on the pipe using the sizing body, section by section. Each section may have the length of the sizing body and the sections overlap over at least half their length. The length of the sections and their rate of overlap may be adjusted.

As previously:
  the overlap of the sections enables consideration to be given to the any slight curvature in the pipe. There may, for example, be an overlap of at least 50%, preferably up to 90%.
  The pipe is considered traversable as a whole if all the sections examined are traversable by the sizing body. The pipe is considered non-traversable if a section blocks completely. If one or more sections examined (or the transitions between them) are at the sticking limit, the pipe must "be inspected".

The above process determines, at the outlet:
1/ whether or not the sizing body passes into the pipe ("pass" or "do not pass" penalty)
2/ in the case of a blockage, the blocking positions (coil number and section identifier, whichever the case);
3/ and in all cases the largest sizing body diameter that can pass into the tested pipe.

This process enables the analysis calculations in the 3D space to be significantly reduced, taking into account every detail of information on the internal shape of the pipe. It requires very little calculation time. This is vital because the purpose of the processing is to be applied in the factory in real time and adjusted to the rate of production.

From a generic viewpoint the above process is based on the coordinates of points on the inner surface of the pipe as measured, for example, by ultrasound. A shape with straight generating lines which is inscribed inside the inner surface of the pipe is sought. And it determines whether the sizing body passes into this shape with straight generating lines.

In the embodiment described this is carried out advantageously by condensing the 3D measurement data in the form of 2D data defined by coils and related to a central point of each coil, then by re-sorting these 2D data into sub-assemblies each corresponding to quasi-diameters essentially parallel with each other. In each sub-assembly two straight lines are then sought which lie flush on the inside with the ends of the quasi-diameters at various points. On all the sub-assemblies this provides a shape with straight generating lines from which it can be determined whether the sizing body passes or does not pass through, or is the "limit".

According to the prior art work is generally done on a pipe provided with its end connections/threads. On the other hand, the embodiments of the invention described above operate in principle on a pipe which has not yet been provided with its end connections/threads. However, it would be worth considering using them on a pipe provided with its end connections/threads. In this case we could just examine the sections at the two ends of the pipe.

The invention claimed is:

1. A method aiding production control of steel pipes, comprising:
   a) acquiring measuring data representative of physical measurements of a geometry of a steel pipe taken on an outside thereof;
   b) from the measurement data, generating converted measurement data to form a three-dimensional representation, by pixels, of an inner wall of the pipe, over a longitudinal area of the pipe, the three-dimensional representation being related to a chosen system of coordinates having a point of origin and an axis that are marked relative to the pipe;
   c) preparing template data representative of an overall geometry of a sizing body, the template data being applicable in the chosen system of coordinates;
   d) considering a first section of the pipe for which converted measurement data are available, and determining from the converted measurement data and template data a critical value representative of a margin of passage of a sizing body inside the first section of the pipe;
   e) selectively repeating the considering d) for other pipe sections offset relative to each other by an overlap; and
   f) establishing a diagnostic of traversability of the longitudinal area of the pipe by the sizing body from critical values obtained in the considering d) and the selectively repeating e), and relative positions of the sections of successive pipes.

2. The method according to claim 1, wherein the measurement data comprises measurements relating to an outer circumference of the pipe and measurements relating to its wall thickness, taken on a pipe whose movement includes a longitudinal translation.

3. The method according to claim 2, wherein the measurements relating to the outer circumference of the pipe are taken by laser sensors, while the measurements relating to its wall thickness are taken by ultrasonic sensors connected to the pipe by a liquid transmission medium.

4. A method according to claim 3, wherein the ultrasonic sensors are mounted so that they are floating so that they remain in interaction with the pipe, and a system is provided for measuring relative position of the laser sensors relative to the ultrasonic sensors.

5. A method according to claim 2, wherein the measurements relating to the outer circumference of the pipe and the measurements relating to its wall thickness are taken simultaneously by ultrasonic sensors interacting with a water box traversed by the pipe.

6. A method according to claim 5, wherein:
   the considering d) comprises determination of a shape with straight generating lines which is inscribed inside an inner surface of the pipe, section by section; and
   the selectively repeating e) comprises a test to ensure the sizing body passes into the shape with straight generating lines of each section considered.

7. A method according to claim 1, wherein:
   in the processing c) the template data comprises an overall outside diameter of the sizing body;
   the considering d) comprises:
   d1) determining a cylinder inscribed inside the pipe section, and
   d2) determining the difference between the diameter of the inscribed cylinder and the overall diameter of the sizing body, as the critical value, and
   the selectively repeating e) comprises, for each pair of adjacent pipe sections, establishment of a possibility of passage from one section to a next from the critical value, of angular deviation between axes of the two pipe sections, and of at least one longitudinal dimension of the sizing body.

8. A device aiding the dimensional inspection of steel pipes during production, comprising:
   at least one measuring station arranged to acquire measurement data representative of physical measures taken of a geometry of a steel pipe on an outside thereof, and
   a computer system configured:
     to store template data representative of an overall diameter of a sizing body, the template data being applicable in the chosen system of coordinates;
     from measurement data, to generate converted measurement data to form a three-dimensional representation, by pixels, of at least two pipe sections offset relative to each other with an overlap, the three-dimensional representation being related to a chosen system of coordinates having point of origin and an axis marked relative to the pipe;
     for each pipe section, to determine from its converted measurement data and template data a critical value representative of the margin of passage of the sizing body inside the pipe section, and
     to establish a diagnostic of traversability of the pipe sections by the sizing body from the critical values and relative positions of the pipe sections.

9. The device according to claim 8, wherein the measurement data comprise measurements relating to the outer circumference of the pipe and measurements relating to its wall thickness taken on a pipe whose movement comprises a longitudinal translation.

10. The device according to claim 9, further comprising a laser measuring station for measurements relating to an outer circumference of the pipe, and an ultrasonic sensor station connected to the pipe by a liquid transmission medium for measurements relating to wall thickness of the pipe.

11. The device according to claim 10, wherein the ultrasonic sensors are mounted so that they are floating to remain in interaction with the pipe, and a system is also provided for measuring the relative position of the laser and ultrasonic sensors.

12. The device according to claim 9, wherein the measurements relating to the outer circumference of the pipe and the measurements relating to its wall thickness are taken simultaneously by a measuring station comprising ultrasonic sensors interacting with a water box traversed by the pipe.

13. The device according to claim 12, wherein the computer system is further configured to determine a shape with straight generating lines which is inscribed inside an inner surface of the pipe, section by section, and to test whether the sizing body passes into the shape with straight generating lines or each section considered.

14. The device according to claim 13, wherein the computer is further configured to condense the 3D measurement data in a form of 2D data defined by coils and related to a central point of each coil, then re-sort the 2D data into sub-assemblies, each corresponding to quasi-diameters essentially parallel with each other.

15. The device according to claim 8, wherein:
   the template data includes an overall outside diameter of the sizing body;
   the determination of the critical value includes a search for a cylinder scribed inside the pipe section and determination between a diameter of the inscribed cylinder and an overall diameter of the sizing body as the critical value,
and
establishment of the diagnostic includes, for a pair of adjacent pipe sections, establishment of a possibility of passage from one section to an other from the critical value, of angular deviation between axes of the two pipe sections, and of at least one longitudinal dimension of the sizing body.

* * * * *